United States Patent
Lehmann (10) Patent No.: US 9,278,378 B2
(45) Date of Patent: Mar. 8, 2016

(54) X-RAY DETECTION OF FLAWS IN CONTAINERS AND/OR IN THEIR CONTENTS

(75) Inventor: Martin Lehmann, Wohlen (CH)

(73) Assignee: WILCO AG, Wohlen (CH)

(*) Notice: Subject to any disclaimer, the term of this patent is extended or adjusted under 35 U.S.C. 154(b) by 0 days.

(21) Appl. No.: 14/405,875

(22) PCT Filed: Jun. 13, 2012

(86) PCT No.: PCT/EP2012/061211
§ 371 (c)(1),
(2), (4) Date: Dec. 5, 2014

(87) PCT Pub. No.: WO2013/185816
PCT Pub. Date: Dec. 19, 2013

(65) Prior Publication Data
US 2015/0144538 A1    May 28, 2015

(51) Int. Cl.
*B07C 5/346*  (2006.01)
*B07C 5/34*   (2006.01)
*B07C 5/342*  (2006.01)
*G01N 23/083* (2006.01)
*G01N 23/18*  (2006.01)
*G01N 23/04*  (2006.01)
*B07C 5/36*   (2006.01)

(52) U.S. Cl.
CPC ............. *B07C 5/3416* (2013.01); *B07C 5/3427* (2013.01); *B07C 5/36* (2013.01); *G01N 23/046* (2013.01); *G01N 23/083* (2013.01); *G01N 23/18* (2013.01); *G01N 2223/419* (2013.01)

(58) Field of Classification Search
CPC ...... B07C 5/3416; B07C 5/36; B07C 5/3427; G01N 23/083; G01N 23/046; G01N 23/18; G01N 2223/419
See application file for complete search history.

(56) References Cited

U.S. PATENT DOCUMENTS

| 4,955,227 A | * | 9/1990 | Fujita ..................... B07C 5/124 73/104 |
| 4,989,225 A | * | 1/1991 | Gupta .................. G01N 23/043 378/10 |
| 5,405,015 A | * | 4/1995 | Bhatia ................... B07C 5/3408 209/524 |

(Continued)

FOREIGN PATENT DOCUMENTS

| EP | 0 604 302 A1 | 6/1994 |
| WO | WO 01/57795 A2 | 8/2001 |
| WO | WO 2010/025539 A1 | 3/2010 |

OTHER PUBLICATIONS

International Search Report and Written Opinion dated Mar. 13, 2013; International Application No. PCT/EP2012/061211; International Filing Date: Jun. 13, 2012.

(Continued)

*Primary Examiner* — Prasad Gokhale
(74) *Attorney, Agent, or Firm* — Oliff PLC (57) ABSTRACT

Method and system for x-ray detection of flaws in containers or their contents wherein containers are conveyed on a circular path around a central axis upon which an x-ray source is situated below the plane of the base of the containers. The x-ray source emits x-ray radiation obliquely upwards through the containers to a plurality of imaging x-ray detectors. Analysis of the images provided by these x-ray detectors determines the presence of a flaw in a container or its contents and is used to command a rejection mechanism to reject the container in question.

21 Claims, 5 Drawing Sheets

(56) References Cited

U.S. PATENT DOCUMENTS

| | | |
|---|---|---|
| 6,005,912 A | 12/1999 | Ocleppo |
| 6,028,910 A | 2/2000 | Kirchner |
| 7,106,827 B2 * | 9/2006 | Heuft .................... B07C 5/3408 378/57 |
| 7,164,750 B2 | 1/2007 | Nabors et al. |
| 2006/0056583 A1 * | 3/2006 | Heuft .................... B07C 5/3408 378/57 |
| 2011/0222647 A1 * | 9/2011 | Sugita .................. G01N 23/046 378/8 |

OTHER PUBLICATIONS

International Preliminary Report on Patentability with Written Opinion, Issued Dec. 16, 2014 of PCT/EP/2012/061211, Inter. Filing Date: Jun. 13, 2012.

* cited by examiner

X-RAY DETECTION OF FLAWS IN CONTAINERS AND/OR IN THEIR CONTENTS

RELATED APPLICATIONS

This application is a U.S. national stage application of International Application Number PCT/EP2012/061211 filed Jun. 13, 2012.

TECHNICAL FIELD

The present invention relates to a system and method for detecting flaws in containers and/or in their contents by means of x-ray radiation imaging.

BACKGROUND AND SUMMARY

During manufacture and/or filling of containers, various flaws can occur. For instance, in the case of glass containers such as glass vials, chips and cracks can occur in the containers themselves, and these chips or cracks can result in glass particles or glass shards being included in the interior of the container. In the case of plastic containers, splits, folds, or other discontinuities can occur during moulding of the container. Other flaws can also occur in the contents of containers of any type: foreign objects may be incorporated due to manufacturing errors, and in the case of containers containing food products, agglomerations of bacterial or fungal matter can occur due to microbial contamination. Another example of such flaws in the contents of containers are bent or broken needles in filled syringes. Such flaws can be detected in closed or open containers, whether filled or unfilled.

It is noted that for the purposes of this specification, the term "flawed container" is to be understood as comprising the case in which the container itself contains a flaw, or in which the contents of the container contains a flaw, or both.

It is important to be able to detect such flaws on a production line to prevent potentially harmfully-flawed or even dangerously-flawed products from reaching the consumer.

Visual inspection, or optical-based methods are only suitable for transparent containers, and inspection of the bottom corners of the interior of containers is made more difficult by optical distortion and refraction caused by the material and shape of the container. The container bottom is typically thick, non-planar, and of non-constant cross-section. Nevertheless this is the most critical portion to be inspected due to foreign objects typically accumulating there. Hence over the years, many different approaches for detecting such flaws have been developed using x-rays, which penetrate glass and plastic irrespective of its optical properties in the visible spectral range. Most materials have a degree of opacity to x-rays, enabling flaws including discontinuities and so on to show up on x-ray transmission imaging. For instance in the case of a glass vial with a crack, the discontinuity caused by the crack will reflect and/or refract the x-ray radiation, which can then be detected. Likewise, a thin section in a plastic container will absorb less x-ray radiation than a thicker section, and will thus be detectable. Furthermore, foreign objects in the container contents will reflect and/or refract and/or absorb x-rays and will likewise be detectable.

Several prior art flaw detecting methods and systems for containers using x-rays are discussed below:

EP 0 604 302 shows a method of x-ray analysis of objects passed on a circular track between an x-ray source and a single detector consisting of a conversion screen and a camera. This method would appear to result in low throughput of objects and poor resolution. Furthermore, the base of the objects will be poorly imaged, since the edges of the track overlap the bases of the objects.

U.S. Pat. No. 6,005,912 shows a method of x-ray analysis of containers incorporating two perpendicular x-ray sources (which may be constituted by a single source emitting two discrete beams) placed at 45° with respect to a line of containers being conveyed between the x-ray sources and respective detectors. Thus two images are taken of each container at 90° of rotation from each other. However, the x-ray source is disposed at the level of a conveyor belt which does not give good coverage of the base of the containers.

U.S. Pat. No. 7,164,750 presents an improvement to the method of U.S. Pat. No. 6,005,912 by situating the x-ray source above the plane of the conveyor so as to achieve improved imaging of the inside of the base of the containers.

U.S. Pat. No. 7,106,827 improves on the above by utilising obliquely-emitted x-rays originating from above and/or below the plane of the base of the containers presented on a linear conveyor belt, so as to better image the inside of the base of the container for the presence of foreign objects. However, a portion of the x-rays must pass through the conveyor belt, which reduces the imaging quality.

Finally, U.S. Pat. No. 4,989,225 shows a CAT scanner for creating dynamically-computed tomographic x-ray images of containers. In one embodiment, containers are passed on a circular path between an x-ray source at the geometric centre of the circular path and a sensor, the containers being additionally rotated around their own axes.

An object of the present invention is thus to overcome at least one of the above-mentioned disadvantages of the prior art, and thereby to provide a system and method for detecting flaws in containers and/or their contents which permits improved detection and higher throughput.

This object is achieved by a system for detecting flaws in containers and/or flaws in their contents, comprising a transport arrangement comprising a transport test path for transporting the containers, the transport test path being arc-shaped about an axis and defining a plane perpendicular to this axis for the movement of the outer surfaces of bases of the containers, i.e. when in use, the outer surfaces of the bases of the containers will travel along this plane. An x-ray source is disposed on the aforementioned axis, and a plurality of imaging x-ray detectors each having a sensing surface, i.e. x-ray detectors capable of forming an image based on received x-ray radiation, are arranged about the axis. By "sensing surface" we understand the surface of a detector which converts x-ray radiation into signals (as in the case of a semiconductor-type direct x-ray detector) or into another type of radiation that will itself be detected (as in the case of a scintillator plate converting x-ray radiation into visible light which is then itself detected by a digital camera or similar). The plurality of detectors permits imaging the containers being tested at various angles so as to obtain good coverage of the containers, and to achieve a good rate of throughput. The plane, x-ray source, and sensing surfaces are arranged such that, when considering each x-ray detector, a straight line which intersects the x-ray source and the x-ray detector in question intersects the plane such that the distance along the line from the x-ray source to the plane be shorter than the distance along the line from the plane to the sensing surface of the x-ray detector in question. Since this line intersects the plane, the x-ray source and the imaging x-ray detectors are situated on opposite sides of the plane. This geometric arrangement ensures good imaging at the detectors since it results in a good degree of magnification of the containers at the imaging x-ray detectors. Furthermore, the system comprises a processing unit with inputs operationally connected to outputs of the imaging x-ray detectors and itself having an output for a signal dependent on x-ray imaging by the imaging x-ray detectors. This output is operationally connected to a control input of a rejection mechanism for rejecting containers detected as having flaws in the containers themselves or in their contents. This combination of features enables accurate testing of containers with a good rate of throughput.

In an embodiment, which may be combined with any subsequently addressed embodiment unless in contradiction, the above-addressed straight line is normal to the sensing surface of the respective imaging x-ray detector. By thus arranging one possible straight line to be drawn as described, distortion at the imaging x-ray detector is minimised.

In an embodiment, which may be combined with any previously or subsequently addressed embodiment unless in contradiction, the x-ray source is tailored to emit x-rays on a single arc, i.e. an unbroken arc. This eliminates the requirement for multiple x-ray sources or complex and potentially fragile shuttering of the x-ray source, thus decreasing complexity and increasing robustness of the system.

In an embodiment, which may be combined with any previously or subsequently addressed embodiment unless in contradiction, the single arc has an opening angle of at least 180°, or of at least 220°, or of at least 270°, or of 360°, as considered in the previously mentioned plane. This permits the radiation to be emitted towards detectors over a wide arc, enabling the use of a large number of detectors in cooperation with a single source.

In an embodiment, which may be combined with any previously or subsequently addressed embodiment unless in contradiction, the distance along the previously mentioned line from the x-ray source to the plane is at most 80%, or at most 60%, or at most 40%, or at most 20% of the distance along that line from the plane to the respective sensing surface. This allows the skilled person to tailor the geometry to achieve the best compromise of magnification and image clarity.

In an embodiment, which may be combined with any previously or subsequently addressed embodiment unless in contradiction, the transport arrangement comprises a plurality of container supports each arranged to contact the base of the container over at most 50% of the area of the base of the container. This ensures that the edges of the base are kept free from interference with the container support, thus maximising the accuracy of the imaging especially of the inside bottom corners of the containers.

In an embodiment, which may be combined with any previously or subsequently addressed embodiment unless in contradiction, the transport arrangement comprises a plurality of container supports each arranged to hold the top of the container, which on the one hand, when used on their own, permits the base of the container to be kept completely free, e.g. in the case when the supports are hanger supports, or on the other hand, when used in combination with supports contacting the container bases, permits a very stable supporting arrangement for the containers.

In an embodiment, which may be combined with any previously or subsequently addressed embodiment unless in contradiction, at least some of the container supports are movable in a direction parallel to the addressed axis, i.e. up and down. This provides one mechanism by which the transport arrangement can pick up containers from e.g. an inlet section of the transport arrangement, such that they can be transported along the transport test path of the transport arrangement.

In an embodiment, which may be combined with any previously or subsequently addressed embodiment unless in contradiction, at least some of the container supports are rotatable about support axes parallel to the addressed axis, e.g. about their own central axes. This enables the containers to be presented to the detectors at different angles so as to image as much of the containers as possible.

Furthermore, the object of the invention is resolved by a method of detecting flaws in containers and/or in their contents, comprising transporting the containers along a transport test path, the transport test path being arc-shaped about an axis and defining a plane perpendicular to said axis for the outer surfaces of bases of said containers, i.e. the plane is defined by the passage of outer surfaces of the bases of the containers as they travel. X-ray radiation is emitted from an x-ray source disposed on the addressed axis, and the emitted x-ray radiation is received at a plurality of imaging x-ray detectors (i.e. x-ray detectors capable of forming an image based on received x-ray radiation) arranged about said axis and having respective sensing surfaces. The plurality of detectors permits imaging the containers being tested at various angles so as to obtain good coverage of the containers, and to achieve a good rate of throughput. The addressed plane, x-ray source and sensing surfaces are mutually arranged such that a respective straight line which intersects the x-ray source and a respective sensing surface intersects the plane such that the distance along the line from said x-ray source to the plane is shorter than the distance along the line from the plane to the respective sensing surface, i.e. the x-ray source and the x-ray detector are disposed on opposite sides of the plane. Images received by the imaging x-ray detectors are processed so as to determine the presence or absence of one or more than one flaws in the container and/or its contents, and the results are assigned to the respective containers. Containers determined as having one or more flaws therein or in their contents are rejected. This method enables accurate testing of containers with a good rate of throughput.

In an embodiment of this method, which may be combined with any subsequently addressed embodiment of the method unless in contradiction, the x-ray radiation is emitted on a single arc. This eliminates the requirement for multiple x-ray sources or complex and potentially fragile shuttering of the x-ray source, thus decreasing complexity and increasing robustness of the system.

In an embodiment of this method, which may be combined with any previously or subsequently addressed embodiment of the method unless in contradiction, the single arc has an opening angle of at least 180°, or of at least 220°, or of at least 270°, or of 360°, considered in the previously-mentioned plane. This permits the radiation to be emitted towards detectors over a wide arc, enabling the use of a large number of detectors and a single source.

In an embodiment of this method, which may be combined with any previously or subsequently addressed embodiment of the method unless in contradiction, the distance along the previously mentioned line from the x-ray source to the plane is at most 80%, or at most 60%, or at most 40%, or at most 20% of the distance along the line from the plane to the respective sensing surface. This allows the skilled person to tailor the geometry to achieve the best compromise of magnification and image clarity dependent on the specific application.

In an embodiment of this method, which may be combined with any previously or subsequently addressed embodiment of the method unless in contradiction, the containers are transported by a transporting arrangement comprising a plurality of supports each arranged to contact the base of a container over at most 50% of the area of the base of the container. Thereby the edges of the base may be kept free from interference with the container support, thus maximising the accuracy of the imaging of the inside bottom corners of the containers.

In an embodiment of this method, which may be combined with any previously or subsequently addressed embodiment of the method unless in contradiction, the containers are transported by a transporting arrangement comprising a plurality of container supports each arranged to hold the top of the container, which on the one hand, when used on their own, permits the base of the container to be kept completely free, e.g. in the case when the supports are e.g. hanging supports, or on the other hand, when used in combination with supports contacting the container bases, permits a very stable supporting arrangement for the containers.

In an embodiment of this method, which may be combined with any previously or subsequently addressed embodiment of the method unless in contradiction, the containers are transported around the transport test path at continuous speed or in a stepwise manner. This presents various operating possibilities, stepwise transport particularly enabling clarity of imaging since the containers can be imaged when stationary.

In an embodiment of this method, which may be combined with any previously or subsequently addressed embodiment of the method unless in contradiction, the containers are rotated about their axes. This can be either at constant angular velocity or stepwise while the containers are transported along the transport test path. This permits imaging the containers from a plurality of angles in a plurality of orientations so as to obtain good coverage of the containers and to reduce the risk of non-detection of a flaw, and also permits tomographic 3-D imaging of the containers.

Finally, the invention relates to a method of manufacturing flaw-free containers, i.e. containers with no detectable flaws in the containers themselves or in the contents thereof, comprising manufacturing filled or unfilled untested containers—this manufacturing possibly also comprising filling of the containers—then testing the containers by any of the above-mentioned methods of detecting flaws. Containers which have not been detected as having flaws therein or in their contents are then accepted as being manufactured flaw-free containers. Containers which have been detected as having flaws therein or in their contents are rejected. This permits reliable manufacture of flaw-free containers.

BRIEF DESCRIPTION OF DRAWINGS

The invention will now be illustrated by means of exemplary embodiments as shown in the attached drawings, which show.

DETAILS DESCRIPTION OF EMBODIMENTS

Figure 1:
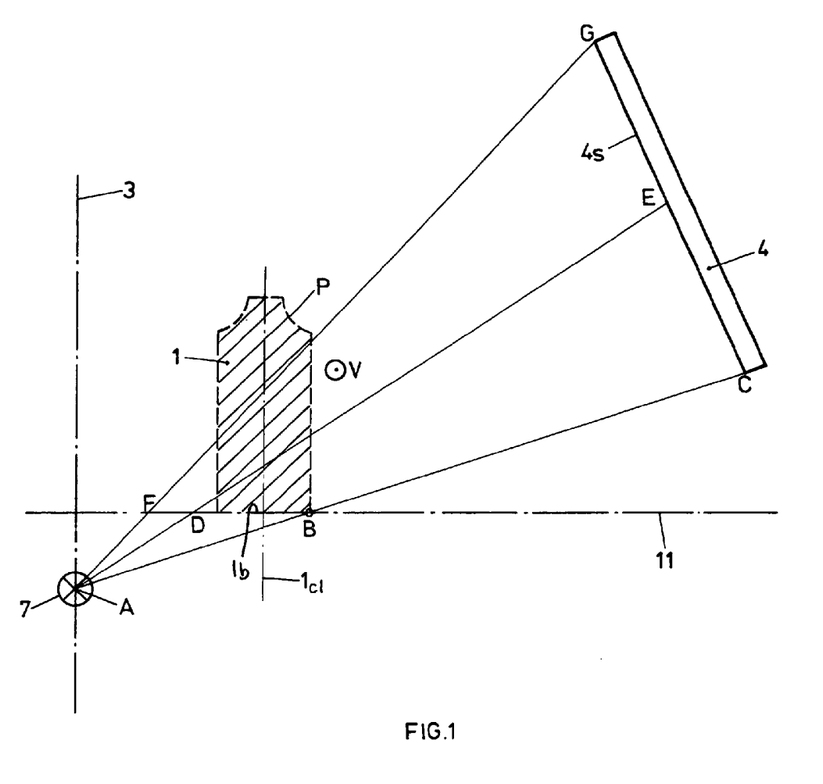
FIG. 1—a schematic illustration of the x-ray source and detector geometry in a vertical section of a part of a system according to the invention and operating the method according to the invention.

FIG. 1 shows an x-ray source 7—substantially a point-source—situated on a vertical axis 3. A transport test path P for containers 1, defined by the volume swept by the containers 1 as they travel following an arc of a circle, e.g. in direction V, is represented here by the cross-section of a single container in a dashed line. Plane 11, along which the exterior surface of the bases 1b of the containers 1 will travel when the system is in operation, is defined by the lower extremity of transport test path P as illustrated in FIG. 1, i.e. by the face of the test path P nearest the x-ray source 7. This plane 11 is perpendicular to the axis 3. The x-ray source 7 is situated below the plane 11 on axis 3. On the opposite side of the plane 11 with respect to the x-ray source 7 is a respective imaging x-ray detector 4, which has a sensing surface 4s facing the x-ray source 7. To illustrate the geometry, a plurality of lines ABC, ADE and AFG have been drawn, originating from x-ray source 7 and terminating at the sensing surface 4s of imaging x-ray detector 4. ABC and AFG are lines intersecting the extremities of the sensing surface 4s of the imaging x-ray detector 4, whereas ADE intersects the sensing surface 4s at an arbitrary point more central to the sensing surface 4s. These lines cross the plane 11 at B, D and F respectively. The length along at least one of the lines within triangle A-G-C, in the present case each line from the x-ray source 7 to the plane 11, i.e. the length of the lines AB, AD and AF, is shorter than the length of the lines from the plane 11 to the sensing surface 4s of the imaging x-ray detector 4, namely the length of the lines BC, DE and FG respectively. In the illustrated example, the length of AB is approximately 60% of the length of BC; the length of AD is approximately 25% of the length of DE; and the length of AF is approximately 15% of the length of FG.

In an embodiment practised today, AB is approximately 13% of BC, and the distance along line ADE (as practiced, the sensing surface 4s of imaging x-ray detector 4 is perpendicular to line ADE) from A to the intersection with the centerline $1_{c1}$ of container 1 is approximately 28% of the distance from the intersection with the centerline $1_{c1}$ of container 1 to E.

This geometry enables the image of the container 1 to be significantly magnified at sensing surface 4s of imaging x-ray detector 4.

The exact geometry required in practice is a compromise between magnification at the sensing surface 4s of imaging x-ray detectors 4—which indicates a greater ratio between the distance between the x-ray source and the imaging x-ray detectors 4 and the distance between the x-ray source 7 and the containers 1—and image clarity, which decreases the closer the containers are to the x-ray source 7, due to diffraction of the x-ray radiation around the features of the containers. Furthermore, the size and shape of the containers being tested must be taken into account, particularly in the specific positioning of the x-ray source 7 (i.e. its distance below plane 11) and the detectors 4.

Figure 2:
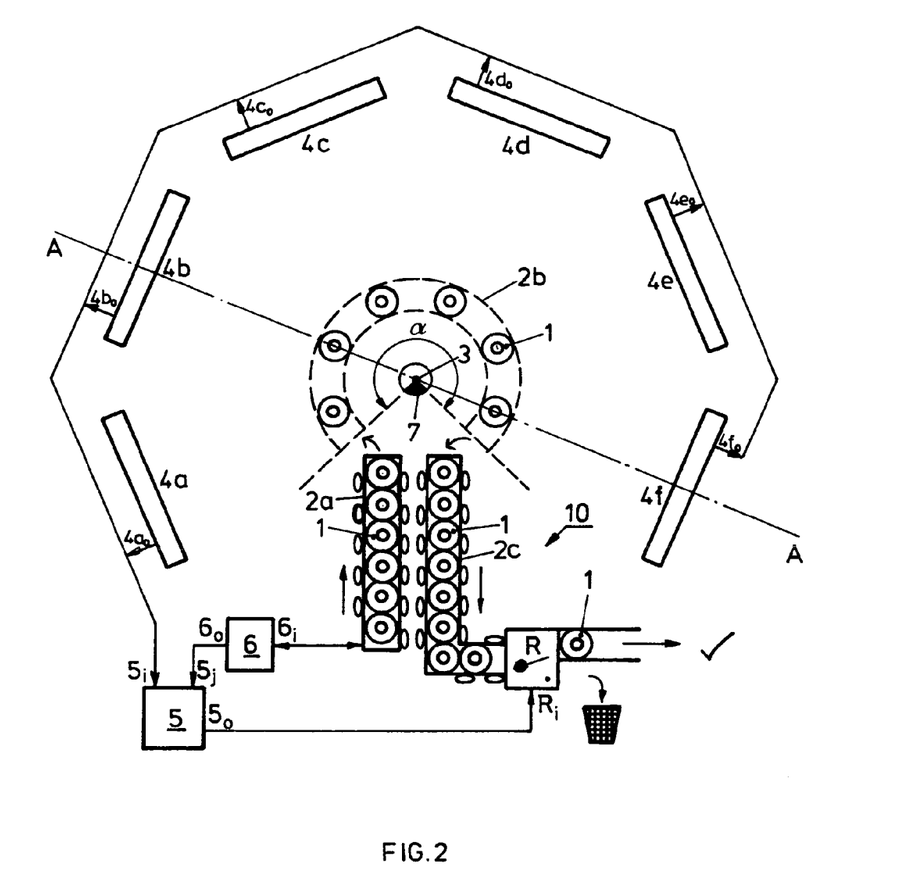
FIG. 2—a schematic plan section of an embodiment of a system according to the invention and operating the method is according to the invention.

FIG. 2 shows schematically a plan top-view of a system according the invention. A plurality of containers 1 travel along a transport path 10. This transport is effected by a transport arrangement comprising an inlet section 2a, a test section 2b along an arc of a circle about axis 3, and an outlet section 2c. The inlet section 2a defines a transport inlet path, the test section 2b defines a transport test path, and the outlet section 2c defines a transport outlet path. Although inlet section 2a and outlet section 2c have been illustrated as linear conveyors, any known convenient arrangement is possible such as arcuate, rotary, or worm-driven as convenient. The test section 2b may transport the containers by any convenient known means, such as a star gear, however a good embodiment is discussed below in greater detail in the context of FIG. 3.

The x-ray source 7 is disposed on the axis 3, below the transport test path, i.e. below plane 11 (see fig. P) defined by the passage of the bases of the containers on the test section 2b when the system is operating. X-ray source 7 is arranged to emit x-rays in a single, unbroken arc with an arc angle α measuring at least 180° considered parallel to the above-mentioned plane 11, which in the illustrated embodiment is approximately 300°. To achieve this, x-ray source may be an omnidirectional x-ray source provided with shielding, or it may be a directional a-beam x-ray source. A radiation shielding arrangement (not illustrated), for instance comprising lead sheeting or concrete blocks or similar x-ray-absorbing material, may be provided to prevent x-rays escaping from the system.

A plurality of imaging x-ray detectors 4a-4f (collectively referenced as 4) are disposed surrounding axis 3, and arranged so as to receive x-ray radiation from x-ray source 7. Although six detectors are illustrated here, any convenient number may be used. These detectors each have a sensing surface 4s (see FIG. 1) arranged facing the x-ray source 7, and may be of any known type, such as direct semiconductor detectors (directly sensitive to x-ray radiation), Flat Panel Detectors based on a scintillating plate and a semiconductor detector (the scintillator converts the x-ray radiation to visible light, and then a conventional semiconductor detector such as a charge-coupled device detector detects this visible light), or any other known type of imaging x-ray detector. Furthermore, each detector 4a-4f may consist of multiple individual detectors arranged as convenient. Outputs $4a_o$-$4f_o$ of the imaging x-ray detectors 4a-4f are connected to input $5_i$ of a processing unit 5. Input $5_i$ may represent a plurality of individual, parallel inputs, one for each imaging x-ray detector 4a-4f, or may be a single, multiplexed input common to all imaging x-ray detectors 4a-4f.

Processing unit 5 analyses the image data taken from the imaging x-ray detectors 4a-4f to identify flaws in the containers 1 or in the contents of containers 1. The image processing required is known to the skilled person. When processing unit 5 detects a flaw based on analysing the image data, it allocates this result to the relevant container based on information provided by transport arrangement controller 6, which may be related to conveyor speed, container count, and so on, and is output by transport arrangement controller 6 at its output $6_o$, and input to processing unit 5 at input $5_j$. Information, such as velocity information or container count information, for instance originating from appropriate sensors, is input to the transport arrangement controller 6 at $6_i$. Processing unit 5 and transport arrangement controller 6 may be implemented in the same unit, and/or sensor information may be input directly into processing unit 5 rather than via transport arrangement controller 6.

Once the result has been allocated to the container with the flaw, processing unit 5 outputs the result at $5_o$ and inputs it into rejection mechanism R at its input $R_i$ so as to actuate rejection mechanism R at the correct moment to reject the flawed container.

Figure 3:
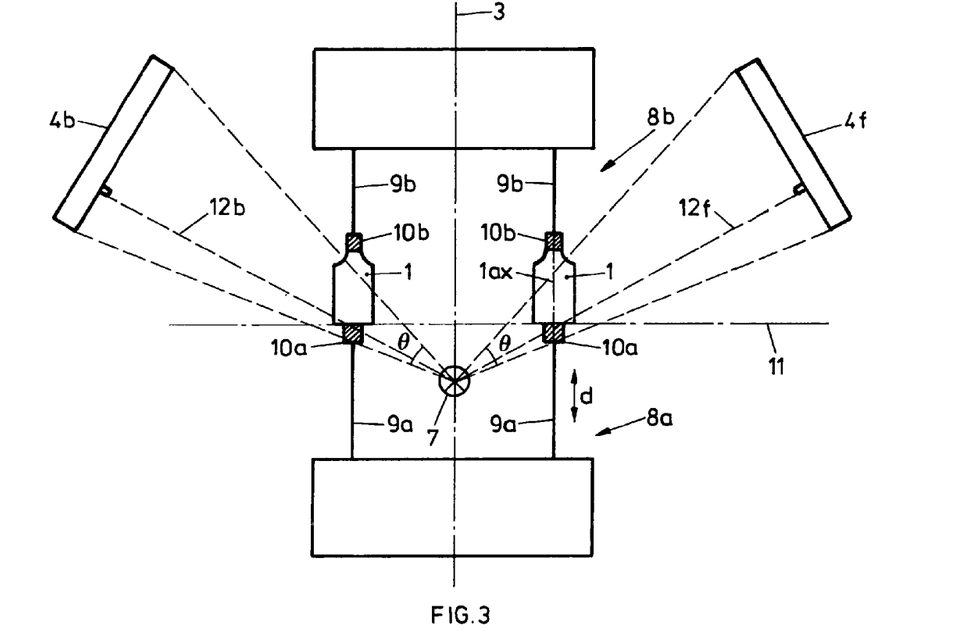
FIG. 3—a schematic section along line A-A of FIG. 1.

FIG. 3 illustrates schematically a section on line A-A of FIG. 2. In this figure, the part of the transport arrangement defining the transport test path is constituted by lower transport arrangement 8a and upper transport arrangement 8b. Each of these arrangements comprises a plurality of rods 9a, 9b movable on a circular path around axis 3, optionally rotatable around their own axes lax. At least the lower rods 9a are movable—d—along their own axes, i.e. up and down on FIG. 3. The rods 9a, 9b may be controlled by any combination of cams, motors, hydraulics or pneumatics as convenient. At the free end of each rod 9a and/or 9b is a support 10a, 10b, for a respectively supporting the top or bottom of each container as appropriate. In the illustrated embodiment, supports 10a, 10b are made from a pad of soft material with a high coefficient of friction, such as natural rubber, silicone rubber, or similar so as to gently clamp the containers 1. Thus, when viewed in context is of the complete system as illustrated in FIG. 2, for instance lower rods 9a of lower transport arrangement 8a can be extended to clamp the containers 1 between lower supports 10a and upper supports 10b, and thereby collect a container 1 from the inlet section 2a. The opposite movement of the rods 9a, 9b as appropriate is carried out to deposit a container 1 on the outlet section 2c. Upper rods 9b may be extendable, or may be of fixed length as convenient. Alternatively, upper rods 9b can be extendable and lower rods 9a fixed.

Figure 3A:
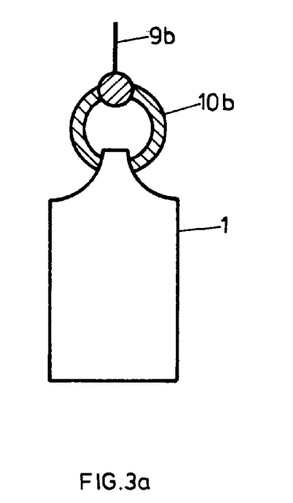
FIGS. 3a-3c—schematic cross-sectional views of various embodiments of container supports.
Figure 3B:
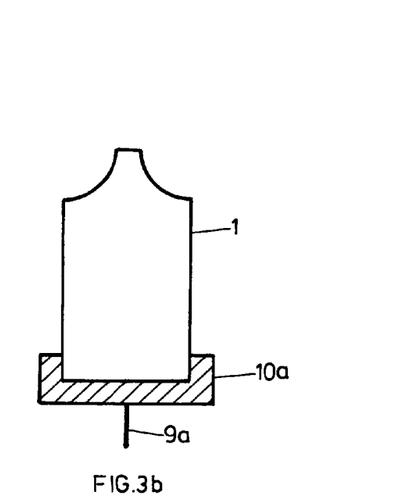
Figure 3C:
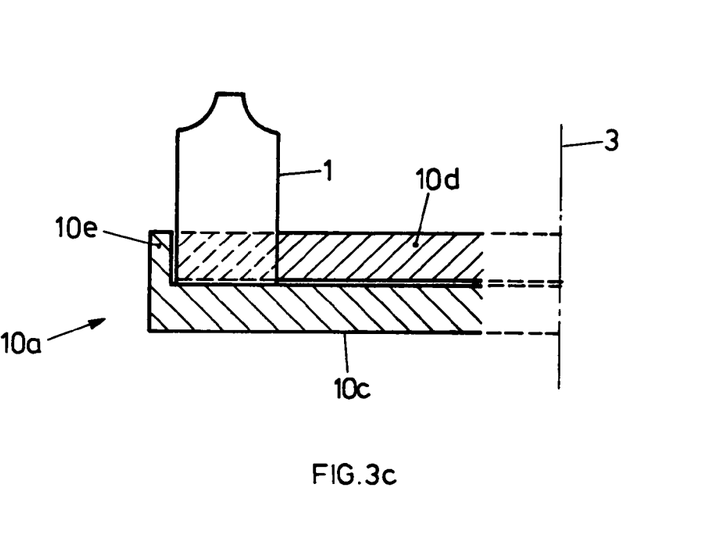

Other alternative embodiments for supporting the containers 1 are illustrated in FIGS. 3a-3c.

In FIG. 3a, lower transport arrangement 8a may be omitted and the rods 9b of the upper transport arrangement 8b are provided with supports 10b comprising gripper from which the container hangs so as to hold each container only at its upper extremity. Alternatively, gripper 10b may be a suction cup arrangement.

In FIG. 3b, upper transport arrangement 8b is omitted, and the lower transport arrangement consists of a cup-type container holder 10a on the free end of rod 9a. As an alternative, this cup-type container holder may comprise a clamping or gripping arrangement.

In FIG. 3c, the lower support 10a consists of a star gear 10d and corresponding stator 10c comprising a circumferential rim 10e, the star gear being arranged to rotate about axis 3, and the containers 1 are received in the interstices between the teeth of the star gear 10d.

As a further alternative, the above-mentioned embodiments may be combined, e.g. the lower supports 10a may be constituted by pads and the upper supports 10b may be constituted by suction cups or grippers, or cup-type lower supports 10a may be paired with suction cup, gripper, or pad-type upper supports 10b.

As discussed above, X-ray source 7 is disposed on central axis 3, and below a plane 11 defined by the path taken by the bases of the containers 1. The imaging x-ray detectors 4a to 4f (FIG. 2) as well as 4b, 4f (FIG. 3), are situated above plane 11. According to FIG. 3, lines 12b and 12f intersect the sensing surfaces of imaging x-ray detectors 4b and 4f respectively, and also intersect the transport path and the x-ray source. In the illustrated embodiment, these lines 12b and 12f are normal to the sensing surfaces of the imaging x-ray detectors 4b and 4f respectively, however this does not need to be the case. The arc angle θ in the vertical plane (i.e. including axis 3) over which the x-ray radiation is emitted may be limited by shielding or similar.

Figure 4:
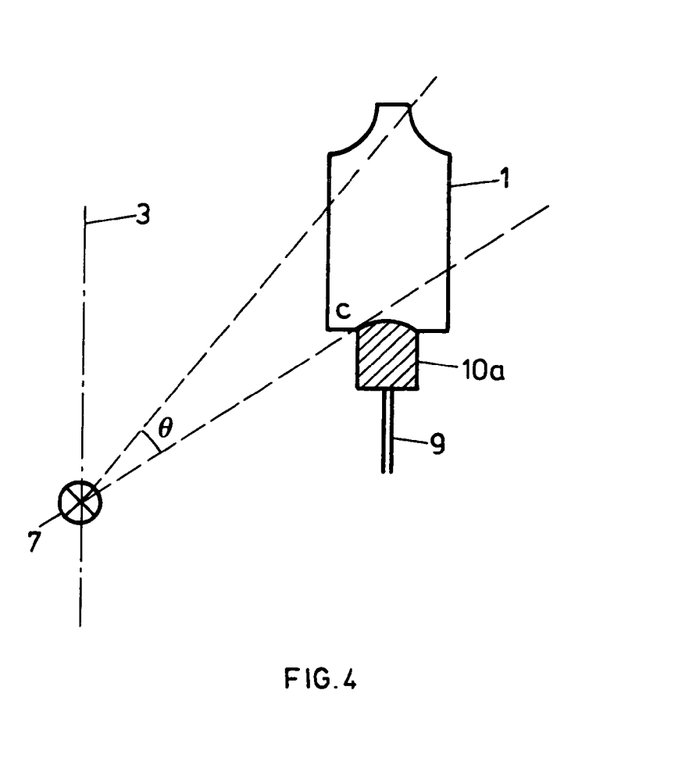
FIG. 4—a close-up view of a geometry of the x-ray source and a container with a further container support.

As is more clearly illustrated on FIG. 4, the illustrated geometry permits the inside bottom corner c of the containers 1 to be investigated by x-rays without interference caused by e.g. lower supports 10a of the transport arrangement. In FIG. 4, container 1 has been illustrated as possessing a concave base, and it is in inside bottom corner c that foreign objects are likely to be found, hence it is the most important portion of container 1 that needs to be investigated. To this end, lower support 10a extends over no more than 50% of the area of the base of the container, leaving the circumference of the base of the container free to be investigated by the x-rays without potential interference and thus loss of image quality due to the lower supports 10a.

The method of operation of the system as described will now be elaborated with reference to FIGS. 2 and 3.

Containers 1 to be tested are introduced along the inlet section 2a of the transport arrangement. When they reach the end of inlet section 2a, they are picked up by transport arrangement 8 and enter test section 2b. Containers 1 are then further transported along test section 2b, between the imaging x-ray detectors 4a-4f and x-ray radiation source 7. This may be carried out according to one of the following schemes:

a. Containers 1 are transported around test section 2b at a substantially constant speed;

b. Containers 1 are transported around test section 2b at a substantially constant speed, and are simultaneously rotated about their own axes at substantially constant angular velocity;

c. Containers 1 are transported around test section 2b stepwise, with each step resulting in the containers being presented to a respective imaging x-ray detector 4a-4f;

d. Containers 1 are transported around test section 2b stepwise, with each step resulting in the containers being presented to a respective imaging x-ray detector 4a-4f, and each container undergoing a stepwise angular rotation about its own axis between being presented to each imaging x-ray detector;

e. Containers 1 are brought into the test section 2b in batches of equal number to the number of imaging x-ray detectors 4a-4f (i.e. batches of six in the case of the illustrated embodiment), are tested and are then output to the outlet section 2c in the same batches;

f. Containers 1 are brought into the test section 2b in batches of equal number to the number of imaging x-ray detectors 4a-4f (i.e. batches of six in the case of the illustrated embodiment), the containers being rotated at either constant angular velocity or stepwise in each position, so as to form images of each container at multiple angles, and are then output to the outlet section 2c in the same batches.

The images obtained by the above schemes can either be processed as two-dimensional images, or may be processed tomographically so as to create 3-D x-ray images of each container.

Once the testing has been completed, the transport arrangement transfers the containers 1 onto its outlet section 2c, on which the containers pass through a rejection mechanism R, which may be of any known type, actuated based on output of processing unit 5 as described above to reject containers which have been detected as having flaws.

Figure 5:
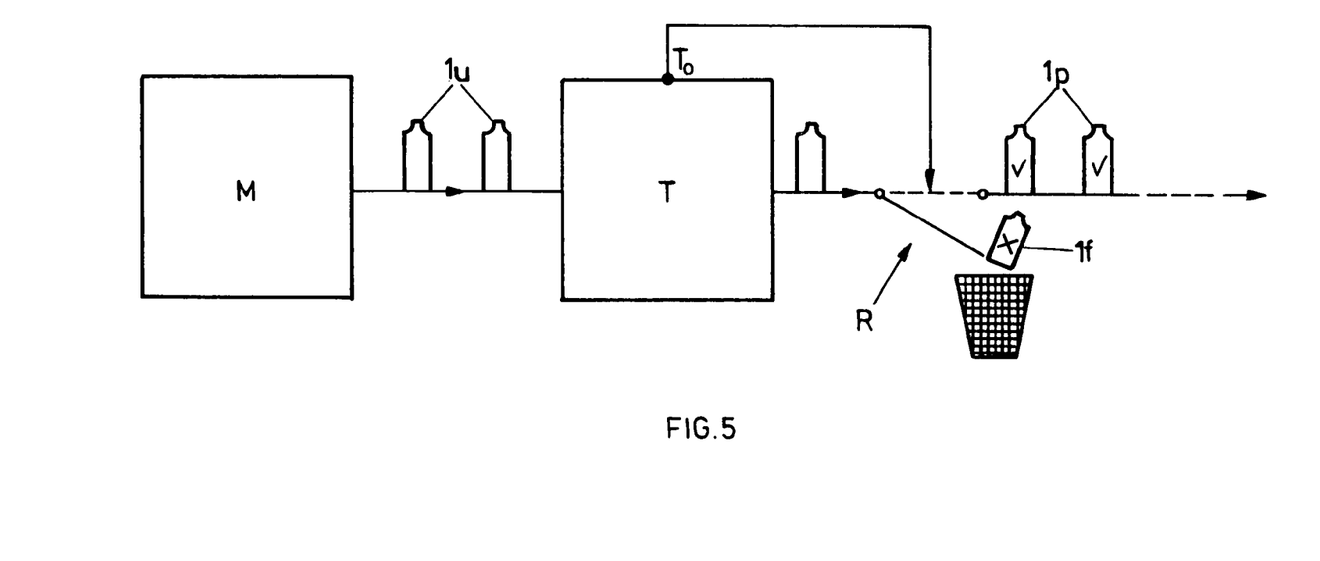
FIG. 5—a schematic, function block representation of a system for manufacturing unflawed containers according to the invention.

FIG. 5 shows schematically and generically a system for manufacturing flaw-free containers. In block M, containers are manufactured and optionally filled, producing untested containers 1u. These untested containers 1u are then passed to block T, where they are tested by any of the above-described methods in any of the above-described systems. Flawed containers if are rejected by rejection mechanism R based on output of the detection system output at $T_o$. Rejection mechanism R may also be incorporated into block T. Unflawed containers 1p, having passed the flaw detection test, are thus considered manufactured and are then passed on for further processing such as further filling if necessary, application of labels, boxing, shipping to customers and so on.

While a full attempt has been made to describe the invention by means of various specific embodiments, these are not to be construed as limiting the scope of the invention, which is defined solely by the scope of the appended claims. In particular, it is noted that all embodiments may be combined as long as the result is not contradictory.

The invention claimed is:

1. A system for detecting flaws in containers or in their contents, comprising:
   a transport arrangement comprising a transport test path for transporting containers, the transport test path being arc-shaped about an axis and defining a plane perpendicular to said axis for the movement of the outer surfaces of bases of said containers;
   an x-ray source disposed on said axis;
   a plurality of imaging x-ray detectors arranged about said axis, each imaging x-ray detector having a sensing surface;
   said plane, x-ray source and sensing surfaces being mutually arranged such that a respective straight line which intersects the x-ray source and a respective sensing surface intersects said plane such that the distance along said line from said x-ray source to said plane is shorter than the distance along said line from said plane to said respective sensing surface;
   a processing unit with inputs operationally connected to outputs of said imaging x-ray detectors and with an output for a signal dependent on x-ray imaging by said detectors;
   a rejection mechanism operationally connected to the transport arrangement and with a control input operationally connected with the output of the processing unit.

2. The system according to claim 1, wherein the straight line is normal to the surface of the respective imaging x-ray detector.

3. The system according to claim 1, wherein the x-ray source is arranged to emit x-rays on a single arc.

4. The system according to claim 3, wherein said single arc has an arc angle selected from the group consisting of at least 180°, at least 220°, at least 270°, and 360°, considered in said plane.

5. The system according to claim 1, wherein the distance along said line from said x-ray source to said plane is selected from the group consisting of at most 80%, at most 60%, at most 40%, and at most 20% of the distance along said line from said plane to said respective sensing surface.

6. The system according to claim 1, wherein the transport arrangement comprises a plurality of container supports each arranged to contact the base of a container over at most 50% of the area of the base of the container.

7. The system according to claim 1, wherein the transport arrangement comprises a plurality of container supports each arranged to hold the top of a container.

8. The system according to claim 1, wherein the transport arrangement comprises a plurality of container supports, and wherein at least some of the container supports are movable in a direction parallel to the said axis.

9. The system according to claim 1, wherein the transport arrangement comprises a plurality of container supports, and wherein at least some of the container supports are rotatable about support axes parallel to said axis.

10. The method of manufacturing flaw-free containers or containers with no flaws in their contents comprising the steps of:
    manufacturing untested filled or unfilled containers;
    testing said containers by the method of claim 1;
    accepting containers which have not been identified as having flaws therein or in their contents as being flaw-free;
    rejecting containers which have been detected as having flaws therein or in their contents.

11. A method of detecting flaws in containers or in their contents comprising:
transporting containers along a transport test path, the transport test path being arc-shaped about an axis and defining a plane perpendicular to said axis for the movement of the outer surfaces of bases of said containers;
emitting x-ray radiation from an x-ray source disposed on said axis;
receiving the emitted x-ray radiation at a plurality of imaging x-ray detectors arranged about said axis, each imaging x-ray detector having a sensing surface, said plane, x-ray source and sensing surfaces being mutually arranged such that a respective straight line which intersects the x-ray source and a respective sensing surface intersects said plane such that the distance along said line from said x-ray source to said plane is shorter than the distance along said line from said plane to said respective sensing surface;
processing images received by the imaging x-ray detectors so as to determine the presence or absence of one or more flaws in at least one of a container and the contents of the container, and
assigning the results to the respective container;
rejecting a container determined as having one or more flaws therein or in its contents.

12. The method according to claim 11, wherein the straight line is
normal to the sensing surface of the respective imaging x-ray detector.

13. The method according to claim 11, comprising emitting said x-ray radiation on a single arc.

14. The method according to claim 13, wherein said single arc has an arc angle selected from the group consisting of at least 180°, at least 220°, at least 270°, and 360°, considered in said plane.

15. The method according to claim 11, wherein the distance along said line from said x-ray source to said plane is selected from the group consisting of at most 80%, at most 60%, at most 40%, and at most 20% of the distance along said line from said plane to said respective sensing surface.

16. The method according to claim 11, comprising transporting the containers by a transporting arrangement comprising a plurality of container supports each arranged to contact the base of a container over at most 50% of the area of the base of the container.

17. The method according to claim 11, comprising transporting the containers by a transporting arrangement comprising a plurality of container supports each arranged to hold the top of a container.

18. The method according to claim 11, wherein the containers are transported around the transport test path at in one of continuous speed and in a stepwise manner.

19. The method according to claim 18 comprising rotating the containers around a support parallel to said axis while transporting the containers along the transport test path.

20. The method according to claim 19, wherein the containers are rotated
at a constant angular velocity around a support parallel to said axis.

21. The method according to claim 19, wherein the containers are rotated stepwise around a support parallel to said axis.

* * * * *